United States Patent [19]

Pissiotas et al.

[11] 4,400,205

[45] Aug. 23, 1983

[54] M-CYANOALKOXY-PHENYLUREAS HAVING HERBICIDAL ACTIVITY

[75] Inventors: Georg Pissiotas, Lörrach, Fed. Rep. of Germany; Otto Rohr, Therwil, Switzerland

[73] Assignee: Ciba-Geigy Corporation, Ardsley, N.Y.

[21] Appl. No.: 340,166

[22] Filed: Jan. 18, 1982

Related U.S. Application Data

[63] Continuation-in-part of Ser. No. 190,144, Sep. 24, 1980, abandoned, which is a continuation-in-part of Ser. No. 132,488, Mar. 21, 1980, abandoned.

[30] Foreign Application Priority Data

Mar. 26, 1979 [CH] Switzerland .................. 2786/79

[51] Int. Cl.³ .................. A01N 47/30; C07C 127/19
[52] U.S. Cl. .................. 71/105; 260/453 RW; 260/465 D
[58] Field of Search .................. 260/465 D, 453 RW; 71/105

[56] References Cited

U.S. PATENT DOCUMENTS 4,046,797 9/1977 Cross .................. 71/105 X

Primary Examiner—Dolph H. Torrence
Attorney, Agent, or Firm—Frederick H. Rabin

[57] ABSTRACT

The m-Cyanoalkoxy-phenylureas of the formula I

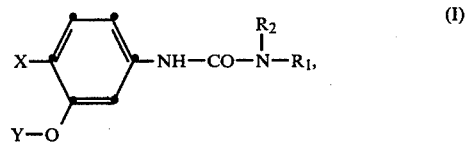

wherein X is hydrogen or halogen, Y—O is a preferably branched-chain cyanoalkoxy group, and —NR₁R₂ is a primary, secondary or heterocyclic amino group, exhibit surprisingly good herbicidal activity against mono- and dicotyledonous plants, with a selective action in crops of maize, cereals, cotton and soya bean, and in the case of some of these compounds also in rape crops.

10 Claims, No Drawings

M-CYANOALKOXY-PHENYLUREAS HAVING HERBICIDAL ACTIVITY

CROSS REFERENCE TO RELATED APPLICATION

This is a continuation-in-part of our application, Ser. No. 190,144, filed Sept. 24th, 1980, now abandoned, which is in turn a continuation-in-part of our application Ser. No. 132,488, filed Mar. 21st, 1980, now abandoned.

The present invention relates to novel m-cyanoalkoxyphenylureas having herbicidal activity, to the production thereof and to compositions containing them, and also to the use of these novel compounds for combating undesired plant growth.

The novel m-cyanoalkoxy-phenylureas correspond to the general formula I

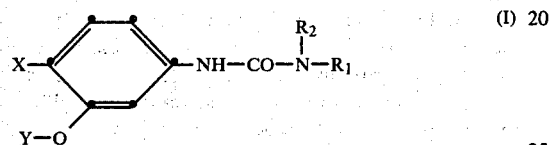

wherein
X is hydrogen or halogen,
Y is $C_2$–$C_4$ cyanoalkyl, unsubstituted or substituted by methoxy,
$R_1$ is $C_1$–$C_4$ alkyl, $C_3$–$C_4$ alkenyl, $C_3$–$C_4$ alkynyl or $C_1$–$C_4$ alkoxy,
$R_2$ is hydrogen, $C_1$–$C_4$ alkyl or $C_3$–$C_4$ alkenyl, or $R_1$ and $R_2$ together with the nitrogen atom to which they are bound form the piperidine ring, which can be substituted by a methyl group.

The preferred alkyl groups $R_1$ and $R_2$ are methyl. The alkylene groups Y are preferably branched e.g. ethylene, isopropylene, iso-, sec- or tert-butylene, X is chlorine or preferably hydrogen.

Among the compounds of formula I, the most active correspond to the group, wherein
X is hydrogen
Y is $C_{2-4}$ cyanoalkyl, unsubstituted or substituted by methoxy
$R_1$ is methyl or methoxy
$R_2$ is methyl.

The compounds of the formula I have marked selective-herbicidal properties in general, and prove particularly advantageous for controlling weeds in crops of useful plants, especially in crops of soya bean, cotton, cereals, maize and sugar beet. Certain of these compounds have a selective action in rape crops. There is achieved however a total herbicidal action when a sufficiently large amount is applied. The novel compounds can be employed both in the pre-emergence process and in the post-emergence process. The applied amounts can vary within wide limits, for example between 0.1 and 10 kg of active substance per hectare, preferably however 0.5 to 5 kg of active substance per hectare are used.

The compositions according to the invention contain, besides the active substance of the formula I, a suitable carrier and/or other additives. Suitable carriers and additives can be either solid or liquid, and they correspond to the substances customarily used in formulation practice, for example they are natural or regenerated mineral substances, solvents, diluents, dispersing agents, emulsifiers, wetting agents, adhesives, thickeners, binders and/or fertilisers.

For use in herbicidal compositions, a compound of the formula I can be processed, in the usual manner of formulation, into the form of a dust, emulsion concentrate, granulate or dispersion, or into the form of a solution or suspension.

A compound of the formula I is produced using methods known per se, for example by reacting an appropriately substituted phenyl of the formula II

with an amine of the formula III

wherein $R_1$, $R_2$, X and Y have the meanings defined under the formula I, whilst A and B are groups which form ureas on undergoing an addition or condensation reaction. One of the two groups A and B is an amine while the other is a urethane, a carbamoyl halide, a urea group or, in particular, the isocyanate group.

Furthermore, it is likewise possible to react m-hydroxyphenylureas of the formula IV

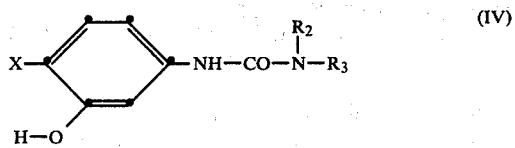

with a cyanoalkyl halide of the formula V

in the presence of an acid-binding agent. In the formulae IV and V, the symbols X and $R_2$ have the meanings defined under the formula I, "alkyl" is a $C_1$–$C_4$ alkylene bridge, preferably branched, which may be substituted by methoxy.

It is not absolutely necessary for a cyanoalkyl halide to be reacted with the m-hydroxyphenylurea, because the cyano group can also be introduced in situ into the molecule, for example by condensing a m-hydroxyphenylurea with a $C_1$–$C_5$ haloalkanecarboxylic acid ester. The ester group is then saponified and the free carboxyl group is subsequently converted, by way of a mixed acid anhydride, with ammonia into the amide, and this is converted in turn by means of a dehydrating agent into a cyanalkoxy group.

These reactions are advantageously performed in organic solvents miscible with water, such as acetone, butanone, dimethylsulfoxide, dimethylformamide, and so forth. The reaction temperatures are between 0° C. and 150° C., preferably between room temperature and the boiling point of the reaction mixture. The reactions are generally carried out under normal pressure, but large amounts can with advantage be produced also in pressure vessels.

The compounds of the formula I have low toxicity for warm-blooded animals; no precautionary measures are thus required for handling these compounds. They have relatively high solubility in customary organic solvents and negligible solubility in water. They can be readily precipitated by addition of water to the reaction solution. Their formulation into liquid herbicidal compositions is possible only with the aid of particular solubility-promoting agents and/or dispersing agents.

The novel active substances of the formula I are stable compounds which are soluble in customary organic solvents, such as alcohols, ethers, ketones, dimethylformamide, dimethylsulfoxide, and the like.

The compositions according to the invention are produced in a manner known per se by the intimate mixing and grinding of active substances of the general formula I with suitable carriers and/or distributing agents, optionally with the addition of antifoaming agents, wetting agents, dispersing agents and/or solvents, all inert to the active substances. The active substances can be obtained and used in the following forms:

solid preparations: dusts, scattering agents, granules, (coated granules, impregnated granules and homogeneous granules);
water-dispersible concentrates of active substance: wettable powders, pastes, emulsions and emulsion concentrates:, and
liquid preparations: solutions.

The concentration of active substance in the compositions according to the invention is 1 to 80 percent by weight, and when being applied the compositions can if necessary contain the active substances also at a lower concentration, such as about 0.05 to 1 percent by weight.

Other biocidal active substances or compositions can be mixed with the compositions according to the invention. For broadening their scope of action, the novel compositions can thus contain, besides the stated compounds of the general formula I, for example insecticides, fungicides, bactericides, fungistatics, bacteriostatics or nematocides, or further herbicides.

The Examples which follow are intended to further illustrate the production of the phenylureas of the formula I according to the invention. Further compounds produced in an analogous manner are listed in the Table following Example 2. The temperature values are given in degrees Centigrade; parts and percentages are by weight, and pressure values are expressed in mm Hg (Torricelli=1.33 millibars). In further Examples are described the processing of the active substances into technically applicable preparations and and also tests designed to demonstrate the herbicidal action of the novel compounds.

EXAMPLE 1

α-[m-(3,3-Dimethylureido)phenoxy]-propionitrile

A mixture of 9 g of N-(m-hydroxyphenyl)-N',N'-dimethylurea, 7.5 g of anhydrous potassium carbonate, 6.7 g of α-bromopropionitrile and 100 ml of methyl ethyl ketone is refluxed for 48 hours with stirring. After cooling, the reaction mixture is filtered, and washed with methyl ethyl ketone. Concentration in vacuo yields 7.6 g of the title product having a melting point of 144°–145°.

EXAMPLE 2

α-[m-(3,3-Dimethylureido)-phenoxy]-isobutyronitrile (a) A mixture of 180.2 g of N-(m-hydroxyphenyl)-N',N'-dimethylurea, 140 g of anhydrous potassium carbonate, 197 g of α-bromo-isobutyric acid ethyl ester and 1000 ml of methyl ethyl ketone is refluxed for 5 days with stirring. After cooling, the reaction mixture is filtered and then washed with methyl ethyl ketone; it is subsequently concentrated in vacuo and treated in a toluene solution with active charcoal. The yield after filtering off the product and concentrating it in vacuo is 119 g of α-]m-(3,3-dimethylureido)-phenoxy]-isobutyric acid ethyl ester, m.p. 62°–63°.

(b) 73 g of the ester described under (a) are dissolved in 330 ml of methanol, and 78 ml of 3.5 N sodium hydroxide solution are added dropwise. Saponification is finished after four hours' stirring at room temperature. The methanol is distilled off and the reaction product is rendered acid with 2 N hydrochloric acid, whereupon the free acid precipitates. The yield is 53.3 g of α-[m-(3,3-dimethylureido)-phenoxy]-isobutyric acid having a melting point of 155°–156°.

This acid can also be produced as follows:

A mixture of 18 g of N-(m-hydroxyphenyl)-N',N'-dimethylurea, 24 g of pulverised sodium hydroxide and 250 ml of acetone is refluxed for about 1 hour. The water bath is then removed and, with vigorous stirring, a mixture of 36 g of chloroform and 50 ml of acetone is added dropwise in such a manner that refluxing is maintained during the addition. After completion of this addition, the reaction mixture is stirred for a further 4 hours under reflux. It is then concentrated by evaporation and the residue is taken up in 300 ml of 2 N sodium hydroxide solution; the insoluble part is extracted with ethyl acetate, and the separated basic-aqueous solution is acidified with dilute hydrochloric acid, whereupon the free acid precipitates. After filtration under suction and drying, the yield is 20 g of α-[m-(3,3-dimethylureido)-phenoxy]-isobutyric acid having a melting point of 196°–197°.

(c) 12 g of the acid produced under (b9 is placed into 50 ml of dioxane, and the whole is mixed with 10.7 ml of tri-n-butylamine, in the course of which a part of the acid goes into solution. The mixture is brought to 10°, and at this temperature there are added dropwise, with stirring, 4.3 ml of chloroformic acid ethyl ester, and stirring is continued for 10 minutes. An excess of ammonia is then introduced likewise at 10°, and the mixture is stirred for 1 hour at room temprature. Finally, the amide is precipitated by the addition of 50 ml of ether and is filtered off with suction. The yield is 10.5 g of α-[m)3,3-dimethylureido)-phenoxy]-isobutyric acid amide having a melting point of 155°–156°.

(d) A mixture of 14 g of the amide described under (c), 29.4 g of triphenylphosphine, 10.8 ml of carbon tetrachloride, 24 ml of triethylamine and 210 ml of ethylene chloride is held for 3 hours, with stirring and under nitrogen, at a bath temperature of 60°. The mixture is subsequently concentrated by evaporation, extracted with ethyl acetate and again concentrated by evaporation. The residue is recrystallised from acetone/hexane to thus yield 10.5 g of α-[m-(3,3-dimethylureido)-phenoxy]-isobutyronitrile having a melting point of 110°.

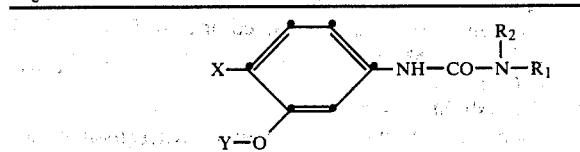

| No. | —O—Y | X | N R₁ R₂ | physical constants |
|-----|------|---|---------|-------------------|
| 1 | OCH(C₃H₇n)CN | H | N(CH₃)₂ | m.p. 138–140° |
| 2 | OCH(CH₃)CN | H | N(CH₃)₂ | m.p. 144–145° |
| 3 | OCH(CH₃)CN | H | N(CH₃)OCH₃ | m.p. 65° |
| 4 | OCH(C₂H₅)CN | H | NHCH₃ | |
| 5 | OCH₂CH(CH₃)CN | H | N(CH₃)₂ | m.p. 142° |
| 6 | OCH(C₂H₅)CN | H | N(CH₃)₂ | m.p. 149–150° |
| 7 | OC(CH₃)₂CN | H | N(CH₃)₂ | m.p. 110° |
| 8 | OC(CH₃)₂CN | H | N(CH₃)OCH₃ | $n_D^{36}$ 1.5240 |
| 9 | OCH(CH₃)CN | H | N(CH₃)ₙC₄H₉ | m.p. 93–94° |
| 10 | OCH(CH₃)CN | H | —N⟨ ⟩—CH₃ (morpholine) | m.p. 119–120° |
| 11 | OCH(C₂H₅)CN | H | N(CH₃)OCH₃ | m.p. 95–96° |
| 12 | OCH(CH₃)CN | Cl | N(CH₃)₂ | m.p. 146–147° |
| 13 | OCH(CH₃)CN | H | N(CH₃)CH(CH₃)C≡CH | |
| 14 | OCH(C₂H₅)CN | H | N(CH₃)CH(CH₃)CH≡CH | |
| 15 | OCH(C₂H₅)CN | H | —N⟨ ⟩—CH₃ (morpholine) | |
| 16 | OCH(C₂H₅)CN | H | N(CH₃)C₄H₉ₙ | |
| 17 | OCH(CN)C₃H₇ₙ | H | N(CH₃)OCH₃ | m.p. 83–85° |
| 18 | OCH(CN)CH₂OCH₃ | H | N(CH₃)OCH₃ | $n_D^{40}$ 1.5323 |

EXAMPLE 3

The processing of compounds of the formula I into preparations of a form suitable in agriculture can be carried out for example according to the following instructions

Wettable powder

The following constituents are used to produce (a) a 70% wettable powder and (b) a 10% wettable powder:

(a)

70 pars of α-[m-(3,3-dimethylureido)-phenoxy]propionitrile,
5 parts of sodium dibutyl-naphthalene sulfonate,
3 parts of naphthalenesulfonic acid/phenolsulfonic acid/formaldehyde condensate (3:2:1),
10 parts of kaolin, and
12 parts of Champagne chalk;

(b)

10 parts of active substance,
3 parts of a mixture of the sodium salts of saturated fatty alcohol sulfates,
5 parts of naphthalenesulfonic acid/formaldehyde condensate, and
82 parts of kaolin.

The given active substance is absorbed onto the appropriate carriers (kaolin and chalk), and the material is subsequently mixed and ground with the other constituents. Wettable powders having excellent wetting and suspension properties are obtained. It is possible to obtain from wettable powders of this type, by dilution with water, suspensions containing 0.1–8% of active substance, and these suspensions are suitable for controlling weeds in crops of cultivated plants.

Paste

The following substances are used to produce a 45% paste:

45 parts of α-[m-(3,3-dimethylureido)-phenoxy]isobutyronitrile,
5 parts of sodium aluminium silicate,
14 parts of cetyl polyglycol ether having 8 mols of ethylene oxide,
1 parts of oleyl polyglycol ether having 5 mols of ethylene oxide,
2 parts of spindle oil,
10 parts of polyethylene glycol, and
23 parts of water.

The active substance is intimately mixed and ground with the additives in apparatus suitable for the purpose. There is obtained a paste from which can be produced, by dilution with water, suspensions of the desired concentration.

Emulsion Concentrate

The following constituents are mixed together to produce a 25% emulsion concentrate:

25 parts of α-[m-(3,3-dimethylureido)-phenoxy]propionitrile,
10 parts of a mixture of nonylphenolpolyoxyethylene or calcium dodecylbenzene sulfonate,
10 parts of cyclohexanone, and 55 parts of xylene.

This concentrate can be diluted with water to give emulsions of suitable concentration, for example 0.1%. Emulsions of this type are suitable for controlling weeds in crops of cultivated plants.

Flowable Preparation

The following substances are used to produce a 45% flowable preparation:
- 45 parts of active substance,
- 5 parts of ethylene glycol,
- 3 parts of octylphenoxypolyethylene glycol having 9–10 mols of ethylene oxide per mol of octylphenol,
- 3 parts of a mixture of aromatic sulfonsulfonic acids condensed with formaldehyde as ammonium salt,
- 1 part of silicone oil in the form of a 75% emulsion,
- 0.1 part of a mixture of 1-(3-chloroallyl)-3,5,7-triazo-azonium-adamantane chloride with sodium carbonate, chloride value at least 11.5%,
- 0.2 part of a bipolymeric thickener having a maximum of 100 nuclei per gram, and
- 42.7 parts of water.

The active substance is mixed and ground with the additives in devices suitable for the purpose. There is obtained a paste from which can be produced, by dilution with water, suspensions of any desired concentration.

EXAMPLE 4

The following tests have served to verify the suitability of the described compositions as herbicides.

Pre-emergence Herbicidal Action (Inhibition of Germination)

Immediately after sowing of the test plants in seed trays in a greenhouse, the surface of the soil is treated with an aqueous dispersion of the active substance, which has been prepared from a 25% emulsion concentrate, and from a 25% wettable powder containing active substance which cannot be produced as an emulsion concentrate owing to inadequate solubility, respectively. Various concentration series are used, corresponding to 2 and 1 kg of active substance per hectare. The seed trays are left in the greenhouse at 22°–25° C. with 50–70% relative humidity, and the test is evaluated after 3 weeks, the results being assessed according to the following scale of ratings:

1 = plants have not germinated or have fully died off,
2–3 = very intense action,
4–6 = moderate action,
7–8 = slight action,
9 = no action (as in the case of untreated control plants).
— plant not tested During these tests, the compounds of formula I were compared with the following known compounds that have similar chemical structure and/or commercial importance
(A) N-(3-chloro-4-methoxy-phenyl)-1,1-dimethylurea "Metoxuron", known from British Pat. No. 1 165 160;
(B) N-(3-chloro-4-cyanomethoxy-phenyl)-N'-methyl-N'-methoxy urea, compound No. 3.5, British Pat. No. 1 294 009;
(C) N-(4-cyanomethoxy-phenyl)-N',N'-dimethyl, urea compound No. 3.3, British Pat. No. 1 294 009;
(D) N-(3-chloro-4-cyanomethoxyphenyl)-N',N'-dimethyl urea, compound No. 3.4, British Pat. No. 1 294 009.

In a first screening test, the compounds were tested at a concentration of 2, 2½, 4 and 5 kg per hectare pre- and post-emergent against a small group of test-plants.

| compound tested | application rate kg/ha | avena fatua | pre-emergent setaria italica | digitaria sanguinalis | sinapis alba | lepidium sp. | solanum nigrum |
|---|---|---|---|---|---|---|---|
| 3 | 4 | 1 | — | 1 | 1 | — | 1 |
|   | 2 | 2 | — | 1 | 1 | — | 1 |
| 6 | 4 | 1 | — | 1 | 1 | — | 1 |
|   | 2 | 1 | — | 1 | 1 | — | 1 |
| 7 | 4 | 1 | — | 1 | 1 | — | 1 |
|   | 2 | 1 | — | 2 | 1 | — | 1 |
| 8 | 4 | 1 | — | 1 | 1 | — | 1 |
|   | 2 | 1 | — | 1 | 1 | — | 1 |
| 11 | 4 | 1 | — | 1 | 1 | — | 1 |
|   | 2 | 1 | — | 2 | 1 | — | 1 |
| A | 4 | 1 | 1 | 1 | 1 | 1 | 1 |
|   | 2 | 1 | 2 | 1 | 1 | 1 | 1 |
| B | 5 | 9 | 9 | — | 6 | 8 | — |
|   | 2.5 | 9 | 9 | — | 7 | 9 | — |
| C | 5 | 8 | 8 | — | 9 | 7 | — |
|   | 2.5 | 8 | 8 | — | 9 | 7 | — |
| D | 5 | 9 | 9 | — | 4 | 6 | — |
|   | 2.5 | 9 | 9 | — | 7 | 7 | — |

Only the compounds of formula I and compound A show satisfactory herbicidal activity.

In a further test, the compounds were tested with a wider variety of plants in lower application rates.

Pre-emergent

| | Compound | | | | | | | | | |
|---|---|---|---|---|---|---|---|---|---|---|
| | No. 2 | | No. 7 | | No. 8 | | No. 11 | | Cmp. A | |
| | Amount Appl'd. (Kg/h) | | | | | | | | | |
| Rating: | 2 | 1 | 2 | 1 | 2 | 1 | 2 | 1 | 2 | 1 |
| barley | 2 | 6 | 1 | 4 | 3 | 4 | 1 | 2 | 2 | 4 |
| barley | 2 | 6 | 1 | 4 | 3 | 4 | 1 | 2 | 2 | 4 |
| wheat | 2 | 4 | 2 | 3 | 2 | 7 | 1 | 2 | 2 | 3 |
| maize | 2 | 2 | 4 | 9 | 9 | 9 | 6 | 9 | 3 | 4 |
| millet | 7 | 7 | 5 | 7 | 4 | 6 | 4 | 7 | 1 | 2 |
| rice | 2 | 4 | 4 | 5 | 5 | 5 | 2 | 2 | 1 | 2 |
| avena fatua | 2 | 2 | 1 | 1 | 1 | 3 | 1 | 1 | 1 | 2 |
| lolium perenne | 2 | 4 | 2 | 2 | 1 | 1 | 1 | 1 | 1 | 1 |
| alopecurus myos. | 2 | 2 | 1 | 1 | 1 | 3 | 1 | 1 | 1 | 2 |
| bromus tectorum rottboellia | 1 | 1 | 1 | 2 | 1 | 2 | 1 | 1 | — | — |
| exaltata | 2 | 3 | 4 | 8 | 5 | 8 | 9 | 9 | 1 | 2 |

-continued

| | Compound | | | | | | | | | |
|---|---|---|---|---|---|---|---|---|---|---|
| | No. 2 | | No. 7 | | No. 8 | | No. 11 | | Cmp. A | |
| | Amount Appl'd. (Kg/h) | | | | | | | | | |
| Rating: | 2 | 1 | 2 | 1 | 2 | 1 | 2 | 1 | 2 | 1 |
| digitaria sang. | 1 | 1 | 1 | 2 | 4 | 5 | 3 | 9 | 1 | 1 |
| echinochloa crus g. | 2 | 5 | 2 | 4 | 1 | 3 | 1 | 1 | 1 | 1 |
| soya bean | 2 | 2 | 2 | 5 | 4 | 8 | 9 | 9 | 1 | 2 |
| cotton | 8 | 8 | 9 | 9 | 8 | 9 | 3 | 9 | 1 | 6 |
| beta sativa | 2 | 2 | 1 | 1 | 1 | 1 | 1 | 1 | 1 | 1 |
| sida spinosa | 1 | 1 | 1 | 1 | 1 | 1 | 1 | 1 | — | — |
| sesbania exaltata | 1 | 1 | 1 | 1 | 1 | 1 | 1 | 2 | 1 | 1 |
| amarantus retroflexus | 1 | 1 | 1 | 2 | 1 | 1 | 1 | 1 | 1 | 1 |
| sinapis alba | 1 | 2 | 1 | 1 | 1 | 1 | 1 | 1 | 1 | 1 |
| ipomoea purpurea | 1 | 2 | 1 | 1 | 1 | 1 | 2 | 2 | 1 | 1 |
| galium aparine | 3 | 4 | 3 | 6 | 2 | 7 | 2 | 5 | 1 | 1 |
| chrysanthemum leucum | 1 | 1 | 1 | 1 | 6 | 8 | 1 | 1 | 2 | 2 |
| abutilon sp. | 1 | 1 | 1 | 1 | 1 | 1 | 1 | 1 | — | — |
| solanum nigrum | 1 | 1 | 1 | 1 | 1 | 1 | 1 | 1 | 1 | 1 |

In this test, the compounds of formula I show good selectivity towards the crops maize, millet and cotton.

Post-emergence Herbicidal Action (Contact Herbicide)

A largish number (at least 7) of weeds and of cultivated plants, both monocotyledonous and dicotyledonous, are sprayed after emergence (in the 4- to 6-leaf stage) with an aqueous active-substance dispersion in dosages of 0.5, 1, 2 and 4 kg of active substance per hectare, and the plants are kept at 24°–26° C. with 45–60% relative humidity. The test is evaluated at least 15 days after the treatment, and the results are assessed as in the pre-emergence test, using the same scale of ratings.

In this test too, the compounds of the formula I demonstrated an excellent action against the broad-leaved weeds and against the majority of gramineous weeds, the cultivated plant maize, the cereal varieties barley, millet and rice, as well as cotton and soya bean remaining undamaged or not being damaged until the applied amounts are increased.

The results from these tests are summarised in the tables which follow.

| compound tested | application rate kg/ha | post-emergent | | | | | |
|---|---|---|---|---|---|---|---|
| | | avena fatua | setaria italica | digitaria sanguinalis | sinapis alba | lepidium sp. | solanum nigrum |
| 3 | 4 | 1 | — | 1 | 1 | — | 1 |
| | 2 | 2 | — | 1 | 1 | — | 1 |
| 6 | 4 | 1 | — | 1 | 1 | — | 1 |
| | 2 | 1 | — | 1 | 1 | — | 1 |
| 7 | 4 | 1 | — | 1 | 1 | — | 1 |
| | 2 | 1 | — | 2 | 1 | — | 1 |
| 8 | 4 | 1 | — | 1 | 1 | — | 1 |
| | 2 | 1 | — | 1 | 1 | — | 1 |
| 11 | 4 | 1 | — | 1 | 1 | — | 1 |
| | 2 | 1 | — | 2 | 1 | — | 1 |
| A | 4 | 1 | 1 | 2 | 1 | 1 | — |
| | 2 | 2 | 1 | 3 | 1 | 2 | — |
| B | 5 | 9 | 9 | — | 6 | 8 | — |
| | 2.5 | 9 | 9 | — | 7 | 9 | — |
| C | 5 | 8 | 8 | — | 9 | 7 | — |
| | 2.5 | 8 | 8 | — | 9 | 7 | — |
| D | 5 | 9 | 9 | — | 4 | 6 | — |
| | 2.5 | 9 | 9 | — | 7 | 7 | — |

Also in this screening-test, only the compounds of formula I and A showed satisfactory herbicidal activity.

These compounds were tested with a further variety of plants in lower application rates.

Post-emergence

| | Compound No. | | | | | |
|---|---|---|---|---|---|---|
| | 3 | 6 | 7 | 8 | 11 | A |
| | applied amount in kg/hectare | | | | | |
| plant | 21 | 21 | 21 | 21 | 21 | 21 |
| barley | 25 | 13 | 23 | 22 | 27 | 57 |
| wheat | 27 | 12 | 22 | 24 | 23 | 99 |
| maize | 79 | 69 | 99 | 99 | 89 | 56 |
| millet | 46 | 79 | 47 | 22 | 99 | 49 |
| rice | 23 | 12 | 34 | 23 | 12 | 22 |
| avena fatua | 24 | 11 | 12 | 11 | 12 | 26 |
| lolium perenne | 14 | 12 | 67 | 12 | 18 | 22 |
| alopecurus myos. | 26 | 11 | 33 | 34 | 12 | 44 |
| bromus tectorum | 23 | 24 | 33 | 22 | 27 | — |
| cyperus rotundus | 44 | 34 | 67 | 88 | 46 | 34 |
| rottboellia exaltata | 11 | 69 | 37 | 11 | 99 | 28 |
| digitaria sang. | 11 | 12 | 23 | 11 | 23 | 34 |
| echinochloa crus g. | 22 | 13 | 33 | 22 | 26 | 12 |
| soya bean | 34 | 78 | 11 | 11 | 89 | 24 |
| cotton | 11 | 47 | 67 | 12 | 12 | 23 |
| sugar beet | 11 | 12 | 12 | 11 | 11 | 12 |
| sida spinosa | 11 | 22 | 11 | 11 | 11 | — |
| exaltata | 11 | 12 | 11 | 11 | 11 | 13 |
| amarantus retroflexus | 11 | 12 | 11 | 11 | 22 | 66 |
| sinapis alba | 11 | 11 | 11 | 11 | 11 | 12 |
| ipomoea purpurea | 22 | 12 | 11 | 11 | 22 | 11 |
| galium aparine | 13 | 78 | 77 | 12 | 14 | 66 |
| chrysanthemum leucum | 11 | 12 | 22 | 12 | 11 | — |
| abutilon sp. | 11 | 11 | 11 | 11 | 11 | — |
| solanum nigrum | 11 | 11 | 11 | 11 | 11 | — |

What is claimed is:

1. A compound of the formula:

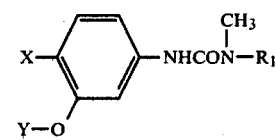

wherein
X is hydrogen or chloro;
$R_1$ is methyl or methoxy; and
Y is a cyanoalkyl group of the formula:

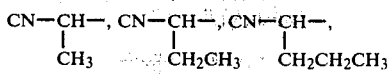

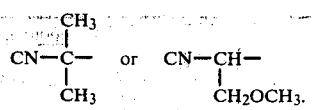

2. A compound according to claim 1 wherein X is hydrogen.

3. α-[m-(3,3-Dimethylureido)-phenoxy]-propionitrile according to claim 1.

4. α-[m-(3,3-Dimethylureido)-phenoxy]-isobutyronitrile according to claim 1.

5. α-[m-(3-Methyl-3-methoxyureido)-phenoxy]-isobutyronitrile according to claim 1.

6. α-[m-(3,3-Dimethylureido)-phenoxy]-isobutyronitrile according to claim 1.

7. α-[m-(3-Methyl-3-methoxyureido)-phenoxy]-butyronitrile according to claim 1.

8. A herbicidal composition comprising an effective amount of a compound according to claim 1 and an inert carrier therefor.

9. A method for controlling undesired plant growth, which comprises treating an area where plant-growth has to be controlled, with an effective amount of a m-cyanoalkoxyphenylurea of the formula I, according to claim 1.

10. A method for selectively controlling weeds in culture crops of maize, cereal, cotton, soya bean and rape, which comprises treating areas, where such crops are sown or growing, with an effective amount of a m-cyanoalkoxyphenylurea of the formula I, according to claim 1.

* * * * *